United States Patent
Olson et al.

(10) Patent No.: US 11,813,286 B2
(45) Date of Patent: *Nov. 14, 2023

(54) COMPOSITION AND THERAPY FOR TREATMENT OF GAG REFLEXES

(71) Applicant: ORION INNOVATIONS INC., St. George, UT (US)

(72) Inventors: Robert Olson, Salmon, ID (US); Deshka Olson, Salmon, ID (US); Wayne Provost, Ivins,, UT (US)

(73) Assignee: ORION INNOVATIONS INC., St. George, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/937,665

(22) Filed: Oct. 3, 2022

(65) Prior Publication Data

US 2023/0024303 A1  Jan. 26, 2023

Related U.S. Application Data

(63) Continuation of application No. 17/315,164, filed on May 7, 2021, now Pat. No. 11,458,162, which is a continuation of application No. 17/100,677, filed on Nov. 20, 2020, now abandoned.

(60) Provisional application No. 62/954,966, filed on Dec. 30, 2019.

(51) Int. Cl.

| | | |
|---|---|---|
| *A61K 33/14* | (2006.01) | |
| *A61K 9/00* | (2006.01) | |
| *A61K 9/14* | (2006.01) | |
| *A61K 9/20* | (2006.01) | |
| *A61K 9/70* | (2006.01) | |
| *A61K 47/12* | (2006.01) | |
| *A61P 1/00* | (2006.01) | |
| *A61P 43/00* | (2006.01) | |

(52) U.S. Cl.
CPC ............ *A61K 33/14* (2013.01); *A61K 9/0056* (2013.01); *A61K 9/14* (2013.01); *A61K 9/20* (2013.01); *A61K 9/70* (2013.01); *A61K 9/7007* (2013.01); *A61K 47/12* (2013.01); *A61P 1/00* (2018.01); *A61P 43/00* (2018.01); *A61K 9/0095* (2013.01); *A61K 9/145* (2013.01)

(58) Field of Classification Search
None
See application file for complete search history.

(56) References Cited

U.S. PATENT DOCUMENTS

| | | | | |
|---|---|---|---|---|
| 4,068,006 A | * | 1/1978 | Moritz | A23L 27/72 426/806 |
| 4,414,198 A | * | 11/1983 | Michaelson | A23F 5/385 426/590 |
| 11,458,162 B2 | * | 10/2022 | Olson | A61K 9/14 |
| 2003/0044359 A1 | * | 3/2003 | Wuelknitz | A61Q 11/00 424/49 |
| 2004/0037878 A1 | * | 2/2004 | Szamosi | A61K 9/2031 424/465 |
| 2013/0142839 A1 | * | 6/2013 | Levine | A61K 9/0056 424/729 |
| 2021/0069097 A1 | * | 3/2021 | Lindbo | A23G 3/50 |
| 2022/0202734 A1 | * | 6/2022 | Kim | C09D 139/06 |

OTHER PUBLICATIONS

Pine ("Tips and tricks: Preventing activation of gag reflex when exposing radiographs", an internet article (published on Sep. 1, 2018) obtained from the website: https://www.rdhmag.com/patient-care/article/16408078/tips-and-tricks-preventing-activation-of-gag-reflex-when-exposing-radiographs) (Year: 2018).*

"How to Take Supplements without Gagging or Getting Them Caught In Your Throat", Naturally Unbridled Wellness (Mar. 1, 2014) (an internet article obtained from the website: https://naturallyunbridled.com/articles/pills-get-caught-in-throat/) (Year: 2014).*

English abstract for JP2004-256120 (Fukuda et al) (Year: 2004).*

Koon ("A breakdown of dosage forms", an internet article published on Apr. 25, 2017 and obtained at the website: https://www.naturalproductsinsider.com/contract-manufacturing/breakdown-dosage-forms) (Year: 2017).*

Reade's Bulk Density Chart (obtained from the website: https://www.reade.com/bulk-density-chart2 ) (date unknown).*

* cited by examiner

*Primary Examiner* — Sin J Lee

(74) *Attorney, Agent, or Firm* — GURR BRANDE & SPENDLOVE, PLLC; Robert A. Gurr

(57) ABSTRACT

The present invention relates to compositions and methods for controlling a gag reflex in a patient.

1 Claim, No Drawings

COMPOSITION AND THERAPY FOR TREATMENT OF GAG REFLEXES

CROSS-REFERENCE TO RELATED APPLICATIONS

This application is a continuation of U.S. application Ser. No. 17/315,164, filed on May 7, 2021, which was a continuation of U.S. application Ser. No. 17/100,677, filed on Nov. 20, 2020, which claimed the benefit of U.S. Provisional Application Ser. No. 62/954,966, filed on Dec. 30, 2019, all of which are incorporated herein by reference.

BACKGROUND OF THE INVENTION

The pharyngeal reflex, gag reflex, or laryngeal spasm (collectively referred to herein as "gag reflex") is a reflex contraction in the back of the throat induced by touching the roof of the mouth, the area around the tonsils, the uvula, and the back of the throat. The gag reflux is the end result of a reflex arc comprised of a series of physiological steps that occur in rapid succession to produce the reflex. Generally, a sensory receptor receives an environmental stimulus such as an object reaching nerves in the back of the throat, which in turn sends a message via an afferent nerve to the central nervous system (CNS). The CNS receives this message and sends an appropriate response via an efferent nerve to effector cells located in the same area as the initial stimulus, which carry out an appropriate physical response (i.e., a gag reflex). The gag reflex is a form of coughing, which, along with other aerodigestive reflexes such as reflexive pharyngeal swallowing, prevents objects in the oral cavity from entering the throat except as part of normal swallowing. As such, the gag reflex is an important physiological response to prevent choking.

Gag reflex sensitivity can vary widely. For example, some people lack a gag reflex, while others experience a hypersensitive gag reflex. This hypersensitivity can lead to issues in various situations, such as when attempting to swallow medications in pill form, swallowing large bites of food, or even when undergoing oral examination, such as when visiting the dentist. In many instances, a hypersensitive gag reflex results in choking, retching and vomiting.

Various systems and methods currently exist which attempt to reduce the gag reflex. For example, local anesthetic agents are commonly used to control the gag reflex, wherein the agent numbs the sensory receptors responsible for initiating the gag reflex. In some instances, this method is undesirable and/or ineffective due to the generalized numbing of the patient's oral cavity and throat (which may lead to additional anxiety in the patient). Other medications, such as tranquilizers may also be used to reduce anxiety and tension which may contribute to the gag reflex, however this solution is limited in effectiveness based on the specific needs of the patient, and may be incompatible with other medications taken by the patient. Acupuncture and acupressure techniques also exist for the treatment of gagging, however these methods are time consuming and are not effective for all patients.

U.S. Pat. No. 4,634,591 (Westerman) provides a method of treating or inhibiting gagging or retching in a patient by sublingual application of a soluble tablet comprising electrolytes in the same proportion as they are found in the blood stream and/or gastric secretions of the patient. These electrolytes may include sodium, potassium, calcium, magnesium, chloride, bicarbonate, and phosphate. The method calls for placing the tablet under the patient's tongue for 2-5 minutes so that a substantial portion of the tablet may be dissolved and absorbed into the patient's system. Where the patient is a severe gagger, it may be necessary to follow with a second tablet in order to obtain the necessary result. Therefore, although the formulations of Westerman are reported to suppress and stop the gag reflex, these methods are inefficient, tedious and may be incompatible for use with children and other patients who experience difficulty with sublingual administration.

Thus, while systems and methods for treating the gag reflex currently exist, challenges remain. The present invention meets and overcomes these challenges.

SUMMARY OF EXAMPLE EMBODIMENTS

Any of the features described herein may be combined in order to arrive at a desired configuration in accordance with the explicitly stated and intended operation of the present invention. Use herein of the transitional phrases "in some embodiments" and "in some instances" is not intended to limit the scope of any particular embodiment to a specific feature or set of features disclosed therewith. Rather, the intention of all the various embodiments described herein is to provide frameworks of context in which a specific feature or a set of features may be comprehended and understood in the context of the inventive concept as a whole. Accordingly, the entirety of the present disclosure is to be understood as a body of interchangeable and modular elements that may be selected and combined (in accordance with the requisite purview of one having ordinary skill in the art) to achieve a device, system, or method within the context of the inventive concept, as a whole, disclosed herein.

In a first aspect of the invention, a composition for controlling a gag reflex in the patient is provided, wherein the composition comprises sodium chloride and a souring agent. In some instances, the composition comprises sodium chloride and a souring agent in a ratio of 1:4. In some instances, the composition comprises a powder form. In some instances, the composition comprises a form selected from the group of a powder, a liquid, a dissolving film, and an oral disintegrating tablet. In some instances, a composition is provided comprising citric acid as a souring agent.

In a second aspect of the invention, a method for controlling a gag reflex in a patient is provided comprising steps for: i) preparing a composition according to the present invention; and ii) administering the composition to the tongue of a patient. In some instances, a method of the invention further comprises a step for delaying an oral procedure after the step of administrating the composition to the tongue of the patient. In some instances, a step for delaying the oral procedure comprises a delay of less than 20 seconds. In some instances, a therapeutic effect of a composition of the present invention glass greater than 12 hours.

DETAILED DESCRIPTION OF EXAMPLE EMBODIMENTS

The present invention relates to compositions and methods for controlling a gag reflex in a patient. In particular, the present invention relates to oral compositions that are applied to the patient's tongue just prior to accessing the oral cavity of the patient, especially in a manner which may induce a gag reflex. In general, the compositions of the present invention are rapid-acting oral formulations comprising a mixture of sodium chloride and a souring agent. Without wishing to be bound by any specific theory, it is believed that one potential mechanism by which the present invention operates is the combination of i) increased saliva production resulting from the sodium chloride, and ii) stimulation of the swallowing reflex resulting from the souring agent, wherein these combined physiological reactions mask or otherwise suppress the patient's gag reflex.

A composition in accordance with the present invention comprises sodium chloride. Sodium chloride may be used in any suitable form, including but not limited to powder form, crystalline form, liquid suspension form, and slurry form. In some embodiments, a composition of the present invention comprises sodium chloride in the form of table salt.

A composition in accordance with the present invention further comprises a souring agent. As used herein, the term "souring agent" is understood to describe any compound, ingredient, chemical or other substance that imparts a sour or acidic taste to a patient when placed on the patient's tongue. Souring agents may be used in suitable form, including but not limited to powder form, liquid form, crystalline form, liquid suspension form, and slurry form. Non-limiting examples of souring agents include citric acid, lemon juice, lemon juice powder, lime juice, lime juice powder, amchur, sour plum, sour plum juice, sour plum juice powder, sumac, tamarind, tamarind powder, vinegar, vinegar powder, umeboshi vinegar, umeboshi vinegar powder, verjuice, verjuice powder, and the like. In some embodiments, a composition comprises a mixture of sodium chloride and two or more souring agents. In some embodiments, a composition comprises a mixture of sodium chloride and a single souring agent.

In some embodiments, a composition is provided comprising a mixture of a sodium chloride and a souring agent, wherein the ratio of the two components is selected to provide a therapeutic benefit that suppresses a patient's gag reflex. In some embodiments, a composition is provided comprising a mixture of sodium chloride and a souring agent, wherein the ratio of sodium chloride to souring agent is 20:1, 15:1, 10:1, 9:1, 8:1, 7:1, 6:1, 5:1, 4:1, 3:1, 2:1 or 1:1. In some embodiments, a composition is provided comprising a mixture of sodium chloride and a souring agent, wherein the ratio of souring agent to sodium chloride is 20:1, 15:1, 10:1, 9:1, 8:1, 7:1, 6:1, 5:1, 4:1, 3:1, 2:1 or 1:1.

In some embodiments, a composition is provided comprising sodium chloride and citric acid.

In some embodiments, sodium chloride is present in the composition in an amount of approximately 90 parts, approximately 80 parts, approximately 70 parts, approximately 60 parts, approximately 50 parts, or less than 50 parts by volume based on 100 parts by volume of the composition. In some embodiments, the sodium chloride is present in the composition in an amount of approximately 80 parts by volume based on 100 parts by volume of the composition.

In some embodiments, citric acid is present in the composition in an amount of approximately 5 parts, approximately 10 parts, approximately 15 parts, approximately 20 parts, approximately 25 parts, approximately 30 parts, approximately 35 parts, approximately 40 parts, approximately 45 parts, approximately 50 parts, or greater than 50 parts by volume based on 100 parts by volume of the composition. In some embodiments, the citric acid is present in the composition in an amount of approximately 20 parts by volume based on 100 parts by volume of the composition.

In some embodiments, the sodium chloride is present in the composition in an amount of approximately 80 parts by volume, and citric acid is present in the composition in an amount of approximately 20 parts by volume based on 100 parts by volume of the composition.

In some embodiments, the composition comprises about 15% by weight, about 20% by weight, about 25% by weight, about 30% by weight, about 35% by weight, about 40% by weight, about 45% by weight, about 50% by weight, or greater than 50% by weight sodium chloride relative to the total weight of the composition. In some embodiments, the composition comprises about 38% by weight sodium chloride relative to the total weight of the composition.

In some embodiments, the composition comprises about 90% by weight, about 85% by weight, about 80% by weight, about 75% by weight, about 70% by weight, about 65% by weight, about 60% by weight, about 55% by weight, about 50% by weight, or less than 50% by weight citric acid relative to the total weight of the composition. In some embodiments, the composition comprises about 62% by weight citric acid relative to the total weight of the composition.

In some embodiments, the composition comprises about 38% by weight sodium chloride and about 62% by weight citric acid relative to the total weight of the composition.

In some embodiments, a composition is provided comprising a dry powder form. In some embodiments, the composition is an admixture of sodium chloride and a souring agent in a dry powder form according to one or more ratios disclosed herein. In some instances, the composition is an admixture of sodium chloride and citric acid in a dry powder form.

In some embodiments, a dry powder composition is provided by admixing specific volumes and/or weights of sodium chloride and a souring agent to achieve desired ratios of the components in the final composition. Admixing may be accomplished by machine or may be done manually. In some embodiments, one or more of the composition components is pretreated to achieve a desired physical state of the component prior to admixing the component into the final composition. For example, in some embodiments it is desirable to pretreat one or more of the components to achieve a desired granule size, for example by grinding, pulverizing, and/or filtering the component(s) through a sieve. In some embodiments, one or more processing steps may be required to produce a powdered form of the souring agent, such as dehydrating or freeze drying a liquid form of the souring agent. Some embodiments of the invention may further include additives or other excipients, as discussed below.

In some embodiments, a composition is provided comprising a dissolving film or oral drug strip that rapidly dissolves on the patient's tongue. In some instances, the dissolving film is a polymer comprising sodium chloride and a souring agent, such as, for example, citric acid. In some instances, the dissolving film further comprises one or more excipients selected from the group consisting of strip-forming polymers, plasticizers, sweetening agents, saliva stimulating agents, flavoring agents, coloring agents, stabilizing agents, thickening agents, and other suitable excipients, wherein the excipient is compatible for use in oral pharmaceutical dosage forms.

In some embodiments, a composition is provided comprising an orally disintegrating tablet configured to rapidly dissolve on the patient's tongue. In some embodiments, an orally disintegrating tablet of the present invention is a loose compression comprising sodium chloride and a souring agent, for example, citric acid. In some embodiments, an orally disintegrating tablet of the present invention is provided in a single dosage form in a sealed blister pack to protect the tablet from damage, moisture, and oxidation.

In some embodiments, a composition is provided comprising an oral spray, wherein the spray comprises sodium chloride and a souring agent, such as citric acid, in liquid forms, and wherein the oral spray is configured for application to the patient's tongue.

In some embodiments, a composition is provided comprising an oral paste or ointment comprising sodium chloride and a souring agent, such as citric acid, wherein the oral paste or ointment is configured for application to the patient's tongue.

In some embodiments, a composition is provided comprising a mouthwash comprising sodium chloride and a souring agent, such as citric acid, wherein the mouthwash is configured for application to the patient's tongue by being held in the patient's mouth passively or swilled or swished around the patient's mouth for an effective treatment period. In some embodiments, an effective treatment period is less than one second, approximately one second, approximately 2 second, approximately 3 seconds, approximately 4 seconds, approximately 5 seconds, approximately 6 seconds, approximately 7 seconds, approximately 8 seconds, approximately 9 seconds, approximately 10 seconds, greater than 10 seconds, or less than 20 seconds. In some embodiments, an effective dose of a mouthwash of the present invention is 1 ml, approximately 1 ml, approximately 2 ml, approximately 3 ml, approximately 4 ml, approximately 5 ml, approximately 6 ml, approximately 7 ml, approximately 8 ml, approximately 9 ml, approximately 10 ml, from approximately 10 ml to 20 ml, from approximately 10 ml to 30 ml, from approximately 15 ml to 25 ml, or from approximately 15 ml to 20 ml. In some instances, the patient may swallow the mouthwash following treatment. In some instances, the patient is instructed to spit out the mouthwash following treatment.

In some embodiments, a method for preventing or suppressing a gag reflex is provided, wherein the method comprises applying a composition of the present invention to a patient's tongue just prior to accessing the oral cavity of the patient. For embodiments where the composition is provided in a powder form, the composition may be applied to the patient's tongue by wetting an applicator that is subsequently contacted with the powdered composition, wherein the wetted state of the applicator causes a therapeutic amount of the powdered composition to adhere to the wetted applicator. The wetted applicator and adhered powdered composition is then applied to the patient's tongue. In some embodiments, an applicator comprises at least one of a tongue depressor, a cotton swab, a gloved finger, or the patient's ungloved finger. In some embodiments, a measured portion of the powdered composition is applied directly to the patient's tongue.

For embodiments where the composition is provided in a paste, ointment or gel form, the composition is applied to the patient's tongue directly using a suitable applicator. For embodiments where the composition is provided in a liquid form, a metered dose of the composition may be sprayed directly on the patient's tongue. For embodiments where the composition is provided in a dissolving film or orally disintegrating tablet forms, these dosage forms are prepared with therapeutically effective amounts of the composition, wherein these dosage forms are applied directly to the patient's tongue.

Therapeutically effective dosages of the present composition may vary depending upon patient needs and/or a selected dosage form. In some embodiments, a therapeutically effective dosage of a composition of the present invention comprises less than 0.5 grams sodium chloride and less than 0.12 grams citric acid, in a volume of 0.125 teaspoons or 0.616 ml, less than 0.25 grams sodium chloride and less than 0.06 grams citric acid, in a volume of 0.0625 teaspoons 11 or 0.308 ml, less than 0.125 grams sodium chloride and less than 0.003 grams citric acid, in a volume of 0.03 125 teaspoons or 0.154 ml, or less than 0.0625 grams sodium chloride and less than 0.0015 grams citric acid, in a volume of 0.015625 teaspoons or 0.077 ml.

In some embodiments, a method of the present invention comprises a delay between application or administration of the composition to the patient's tongue and accessing the oral cavity of the patient. In some instances, the delay is less than 10 seconds, less than 8 seconds, less than 5 seconds, less than 3 seconds, or less than 1 second. In some embodiments, a therapeutic effect of the composition lasts for greater than 30 minutes, greater than 1 hour, greater than 2 hours, greater than 4 hours, greater than 8 hours, greater than 12 hours, greater than 16 hours, greater than 20 hours, or greater than 24 hours.

EXAMPLES

Anti-Gag Composition

An anti-gag composition was prepared by mixing dry ingredients of sodium chloride and citric acid in a ratio of 1:4. Single dosage amounts of the anti-gag composition were prepared and sealed in individual, single-use containers.

Anti-Gag Treatment

A patient with acute gag sensitivity was treated with an anti-gag composition of the present invention prior to undergoing oral examination as part of dental treatment. A tongue depressor was wetted and contacted with the anti-gag composition, thereby adhering a therapeutically effective amount of the anti-gag composition to the wetted tongue depressor. The tongue depressor and the therapeutically effective amount of the anti-gag composition was then applied to the top surface of the patient's tongue, whereupon the anti-gag composition dissolved on the patient's tongue. Oral examination of the patient commenced within less than 30 seconds 12 of administering the anti-gag composition. The patient was able to undergo oral examination and complete dental treatment Without manifesting a gag reflex.

One of skill in the art will appreciate that the various features and elements of the various embodiments of the present invention may be modified and/or combined Within the spirit of the present invention to provide a composition for preventing or suppressing a gag reflex in a patient. For example, the active agents of the present invention include and/or may be substituted with any compatible analogs or pharmaceutically acceptable salts thereof, including any stereoisomers, including enantiomeric forms and diastereomeric forms, all of which are contemplated Within the scope of this disclosure. Individual stereoisomers of the compounds of the disclosure may, for example, be substantially free of other isomers, or may be admixed, for example, as racemates or with all other, or other selected, stereoisomers, as may apply. The specific ingredient ratios may be adjusted, as disclosed herein, and as may be desired to meet the specific needs of a patient. The inclusion and/or exclusion of various excipients are also contemplated Within the scope of this disclosure.

The present invention may be embodied in other specific forms Without departing from its structures, methods, or other essential characteristics as broadly described herein and claimed hereinafter. Therefore, the described embodiments are to be considered in all respects only as illustrative, and not restrictive. The scope of the invention is, therefore, indicated by the appended claims, rather than by the foregoing description. All changes that come Within the meaning and range of equivalency of the claims are to be embraced Within their scope.

What is claimed is:

1. A composition for controlling a gag reflex in a patient, the composition consisting of sodium chloride and citric acid in a ratio of 3:1 by volume, wherein the composition is in a powder form.

* * * * *